(12) United States Patent
Tobita

(10) Patent No.: US 7,947,260 B2
(45) Date of Patent: May 24, 2011

(54) LOW TEMPERATURE-STABLE CREAMY WASH COMPOSITION

(75) Inventor: Kazuhiko Tobita, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 706 days.

(21) Appl. No.: 11/770,113

(22) Filed: Jun. 28, 2007

(65) Prior Publication Data

US 2008/0008672 A1 Jan. 10, 2008

(30) Foreign Application Priority Data

Jul. 7, 2006 (JP) .................................. 2006-188043

(51) Int. Cl.
*A61K 8/30* (2006.01)
(52) U.S. Cl. .................................. 424/70.22; 424/70.31
(58) Field of Classification Search ........................ None
See application file for complete search history.

(56) References Cited

U.S. PATENT DOCUMENTS

| | | | | |
|---|---|---|---|---|
| 5,616,552 A | * | 4/1997 | Yoshihara et al. | 510/490 |
| 5,849,310 A | * | 12/1998 | Trinh et al. | 424/401 |
| 6,288,023 B1 | * | 9/2001 | Honda et al. | 510/490 |
| 6,566,313 B1 | * | 5/2003 | Hohenstein et al. | 510/125 |
| 2007/0037728 A1 | | 2/2007 | Kunieda et al. | |

FOREIGN PATENT DOCUMENTS

| | | |
|---|---|---|
| JP | 62-124200 | 6/1987 |
| JP | 01-294799 | 11/1989 |
| JP | 2003-183152 | 7/2003 |

OTHER PUBLICATIONS

U.S. Appl. No. 11/685,421, filed Mar. 13, 2007, Tobita.
Office Action issued on Dec. 9, 2010, in Chinese Application No. 200710128707.0, with English Translation.
Office Action issued on Dec. 27, 2010, in Korean Application No. 10-2007-0066523, with English Translation.

* cited by examiner

*Primary Examiner* — Tracy Vivlemore
*Assistant Examiner* — Jennifer A Berrios
(74) *Attorney, Agent, or Firm* — Oblon, Spivak, McClelland, Maier & Neustadt, L.L.P.

(57) ABSTRACT

Creamy wash composition containing (A) at least one N-long-chain-acyl acidic amino acid or a salt thereof, (B) at least one polyhydric alcohol, (C) at least one nonionic surfactant, (D) at least one salt of a divalent or higher cation and a monovalent or higher anion, and (E) water are stable at a low temperature and exhibit good foaming properties and a good feeling upon use.

10 Claims, No Drawings

LOW TEMPERATURE-STABLE CREAMY WASH COMPOSITION

CROSS REFERENCES TO RELATED APPLICATIONS

This application claims priority to Japanese Patent Application No. 188043/2006, filed on Jul. 7, 2006, which is incorporated herein by reference in their entireties.

BACKGROUND OF THE INVENTION

1. Field of the Invention

The present invention relates to low temperature-stable creamy wash compositions. The present invention also relates to methods of preparing such a composition. The present invention further relates to methods of washing with such a composition.

2. Discussion of the Background

It has been long known that N-long-chain-acyl acidic amino acids and/or salts thereof are useful as less irritating materials in comparison with a skin or hair wash containing an anionic surfactant such as an alkyl sulfate or an alkyl sulfonate as an active ingredient, which has been generally used.

When an N-long-chain-acyl acidic amino acid and/or a salt thereof having high safety is used in a creamy wash composition of a cleansing foam, a makeup remover, or the like, it has been known that a composition is obtained by containing an N-long-chain-acyl acidic amino acid and/or a salt thereof, a polyhydric alcohol, and water, as essential ingredients (see, JP-A-62-124200). However, such a creamy wash composition is problematic in that it becomes hard at a low temperature and tends to separate at a high temperature. Accordingly, it has not necessarily been said to be a low temperature-stable creamy wash composition.

An example of an approach to eliminate the problem of a creamy wash composition becoming hard at a low temperature is the use of a 2-alkyl-N-carboxymethyl-N-hydroxyethylimidazolinium betaine as an ampholytic surfactant in combination with an N-long-chain-acyl acidic amino acid and a polyhydric alcohol (see, JP-A-1-294799). However, it still becomes hard when stored at a low temperature, and no satisfactory low temperature-stable creamy wash composition has been obtained.

Thus, there remains a need for a low temperature-stable creamy wash composition which contains an N-long-chain-acyl acidic amino acid and/or a salt thereof and a polyhydric alcohol as active ingredients and which is excellent in low temperature stability, without impairment of the foaming properties and/or deterioration of the feeling upon use.

SUMMARY OF THE INVENTION

Accordingly, it is one object of the present invention to provide novel creamy wash compositions.

It is another object of the present invention to provide novel creamy wash compositions, which are stable at low temperature.

It is another object of the present invention to provide novel creamy wash compositions, which are stable at low temperature, without impairment of the foaming properties.

It is another object of the present invention to provide novel creamy wash compositions, which are stable at low temperature, without deterioration of the feeling upon use.

It is another object of the present invention to provide novel methods of preparing such a wash composition.

It is another object of the present invention to provide novel methods of washing with such a wash composition.

These and other objects, which will become apparent during the following detailed description, have been achieved by the inventors' discovery that a desired low temperature-stable creamy wash composition is obtained by mixing (A) an N-long-chain-acyl acidic amino acid and/or its salt, (B) a polyhydric alcohol, (C) a nonionic surfactant, (D) a salt made of a divalent or higher cation and a monovalent or higher anion, and (E) water.

That is, the invention provides the following:

(1) A low temperature-stable creamy wash composition, which comprises:

(A) at least one N-long-chain-acyl acidic amino acid or a salt thereof;

(B) at least one polyhydric alcohol;

(C) at least one nonionic surfactant;

(D) at least one salt of a divalent or higher cation and a monovalent or higher anion; and (E) water.

(2) The low temperature-stable creamy wash composition according to (1), wherein:

said (A) at least one N-long-chain-acyl acidic amino acid or a salt thereof and said (C) at least one nonionic surfactant are present in a weight ratio of from 95:5 to 50:50;

said (A) at least one N-long-chain-acyl acidic amino acid or a salt thereof and said (D) at least one salt of a divalent or higher cation and a monovalent or higher anion are present in a weight ratio of from 99.9:0.1 to 70:30;

said (A) at least one N-long-chain-acyl acidic amino acid or a salt thereof, said (C) at least one nonionic surfactant, and said (D) at least one salt of a divalent or higher cation and a monovalent or higher anion are present in a total amount of from 10 to 40% by weight based on the total weight of said low temperature-stable creamy wash composition; and said (B) at least one polyhydric alcohol is present in an amount of from 10 to 50% by weight based on the total weight of said low temperature-stable creamy wash composition.

(3) The low temperature-stable creamy wash composition according to any of (1) and (2), wherein said (A) at least one N-long-chain-acyl acidic amino acid or a salt thereof comprises at least one N-long-chain-acyl glutamic acid or a salt thereof.

(4) The low temperature-stable creamy wash composition according to any of (1) to (3), wherein said (C) at least one nonionic surfactant comprises at least one monoglyceryl mono-fatty acid ester.

(5) A low temperature-stable creamy wash composition, which comprises:

(A) at least one N-long-chain-acyl acidic amino acid or a salt thereof;

(B) at least one polyhydric alcohol;

(C) at least one nonionic surfactant;

(D) at least one salt of a divalent or higher cation and a monovalent or higher anion; and (E) water, wherein said wash composition has a hardness at 0° C. according to a load test with a Rheometer of from 5 to 250 (g) and a ratio of hardness at 0° C. to hardness at 25° C. of from 0.5 to 2.4.

Thus, it has been possible to obtain a low temperature-stable creamy wash composition which comprises an N-long-chain-acyl acidic amino acid and/or a salt thereof and a polyhydric alcohol as active ingredients without impairing the foaming properties and/or deteriorating the feeling upon use.

DETAILED DESCRIPTION OF THE PREFERRED EMBODIMENTS

In the present invention, the term "creamy" refers to a state in which a substance has a hand cream-like appearance which is strong in whiteness, soft, smooth, and glossy, can easily be scooped with a fingertip by being filled in a tube or a jar and does not exhinbit dropping or stringing. It is different from a state of a liquid which is fluid when a container is inclined.

Further, the term "low temperature-stable" means a state which still shows appropriate hardness at 0° C. and provides a small change between the hardness at 0° C. and the hardness at 25° C. Specifically, it refers to a state in which the hardness at 0° C. according to a load test (described below) with a Rheometer is from 5 to 250 (g) and the ratio of the hardness at 0° C. to the hardness at 25° C. is from 0.5 to 2.4. A lower hardness at 0° C. is preferable. Specifically, a hardness of from 5 to 150 (g) is especially preferable. A ratio of the hardness at 0° C. to the hardness at 25° C. which is closer to 1 is preferable. Specifically, a ratio of from 0.5 to 1.4 is especially preferable. As a combination of both cases, it is preferable that in the load test with a Rheometer, the hardness at 0° C. is from 5 to 250 (g) and the ratio of the hardness at 0° C. to the hardness at 25° C. is from 0.5 to 2.4. It is especially preferable that in the load test with a Rheometer, the hardness at 0° C. is from 5 to 150 (g) and the ratio of the hardness at 0° C. to the hardness at 25° C. is from 0.5 to 1.4.

A method for measuring hardness of a creamy wash composition is as follows:

A prepared creamy wash composition was filled in a 50 mL-glass vial (diameter 3.5 cm) to a height of 4 cm, and allowed to stand still at 0° C., 25° C., and 40° C. for 24 hours. A load test was conducted using a FUDO RHEOMETER (NRM-2010J-CW) and a flat cylindrical adapter (diameter 1.5 cm) at a table speed of 2 cm/min. A load value (g) after 30 seconds was defined as the hardness of the creamy wash composition at each temperature.

The N-long-chain-acyl acidic amino acid and/or its salt as component (A) used in the present invention may be obtained by a known method. For example, a Schotten-Baumann reaction of an acidic amino acid and a fatty acid halide is a widely known method.

As the acidic amino acid component of component (A), glutamic acid, aspartic acid, and the like are available. In other words, the N-long-chain-acyl acidic amino acid may be a N-long-chain-acyl acidic glutamic acid or a N-long-chain-acyl acidic aspartic acid. These amino acids may be L-isomers, D-isomers, or DL-isomers. These may be used either singly or in admixture of two or more selected from the foregoing group. From the standpoint of good stability and good feeling upon use of a material after acylation, glutamic acid is preferable.

As the acyl group of component (A), linear or branched acyl groups derived from saturated or unsaturated fatty acids having from 8 to 22 carbon atoms are available. Examples of the fatty acids include caprylic acid, capric acid, lauric acid, myristic acid, stearic acid, isostearic acid, palmitic acid, oleic acid, linoleic acid, behenic acid, coconut oil fatty acid, palm fatty acid, hardened tallow fatty acid, and the like. These may be used either singly or in admixture of two or more selected from the foregoing group. Especially in view of obtaining a low temperature-stable creamy wash composition with good foam quality, lauric acid, myristic acid, and palm fatty acid are preferable.

The salt as component (A) is not particularly limited. Examples thereof include inorganic salts of alkali metals such as sodium and potassium, alkaline earth metals such as calcium and magnesium, aluminum and zinc, and organic salts of ammonia, organic amines such as monoethanolamine, diethanolamine, and triethanolamine and basic amino acids such as arginine and lysine. They may be used either singly or in admixture of two or more selected from the foregoing groups. In view of easy procurement, handling, and the like, alkali metal salts, organic amine salts, and basic amino acids are preferable, and sodium, potassium, triethanolamine, and arginine are especially preferable.

The polyhydric alcohol as component (B) is not particularly limited. Examples thereof include glycerin, diglycerin, sorbitol, propylene glycol, dipropylene glycol, butylene glycol, polyethylene glycol, and the like. These may be used either singly or in admixture of two or more selected from the foregoing group. From the standpoint of obtaining a low temperature-stable creamy wash composition having good appearance, glycerin and propylene glycol are preferable, and glycerin is especially preferable.

The nonionic surfactant as component (C) is not particularly limited. Examples thereof include a glyceryl mono-fatty acid ester, a glyceryl di-fatty acid ester, a glyceryl tri-fatty acid ester, a propylene glycol mono-fatty acid ester, a butylene glycol mono-fatty acid ester, a diethylene glycol mono-fatty acid ester, a mono-fatty acid N-methylethanolamide, lauryl glycol hydroxypropyl ether, a polyoxypropylene (1) coconut oil fatty acid monoisopropanolamide, and the like. These may be used either singly or in admixture of two or more selected from the foregoing group. Of these, in view of a low molecular weight and excellent feeling upon use, a glyceryl mono-fatty acid ester, a propylene glycol mono-fatty acid ester, a butylene glycol mono-fatty acid ester, a diethylene glycol mono-fatty acid ester, a mono-fatty acid N-methylethanolamide, lauryl glycol hydroxypropyl ether, and a polyoxypropylene (1) coconut oil fatty acid monoisopropanolamide are preferable, and a glyceryl mono-fatty acid ester is especially preferable.

Specific examples of a glyceryl mono-fatty acid ester include glyceryl monocaprylate, glyceryl monocaprate, glyceryl monolaurate, glyceryl monomyristate, glyceryl monopalmitate, glyceryl monostearate, glyceryl monoisostearate, and the like. These may be used either singly or in admixture of two or more selected from the foregoing group. Of these, glyceryl monocaprylate, glyceryl monocaprate, glyceryl monolaurate, and glyceryl monomyristate are preferable in view of obtaining a low temperature-stable creamy composition with appropriate hardness by a combination of an N-long-chain-acyl acidic amino acid and/or its salt as component (A), a polyhydric alcohol as component (B), a salt made of a divalent or higher cation and a monovalent or higher anion as component (D), and water as component (E). As the fatty acid, a saturated or unsaturated fatty acid having from 8 to 18 carbon atoms is available, and it may have a substituent unless the effects of the invention are impaired. When the carbon number is less than 8, the N-long-chain-acyl amino acid and/or its salt as component (A) are/is less precipitated. When it is more than 16, a creamy wash composition is liable to be hardened. Accordingly, in view of obtaining the low temperature-stable creamy wash composition, the carbon number is preferably from 8 to 14, and in view of maintaining the foaming property, it is more preferably from 10 to 12.

The salt made of the divalent or higher cation and the monovalent or higher anion as component (D) used in the invention is not particularly limited. Examples of the divalent or higher cation include alkaline earth metal ions such as a magnesium ion and a calcium ion, transition metal ions such as a zinc ion, an aluminum ion, an iron ion, and a copper ion, organic basic cations having two or more bases, such as ethylenediamine and propylenediamine, and the like. Examples of the monovalent or higher anion include anions derived from inorganic acids, such as a chlorine ion, a sulfate ion, and a phosphate ion, and anions derived from organic acids such as glutamic acid, aspartic acid, pyrrolidonecarboxylic acid, citric acid, gluconic acid, acetic acid, carbonic acid, and fatty acids. Specific examples thereof include magnesium chloride, calcium chloride, magnesium sulfate, calcium sulfate, magnesium carbonate, calcium carbonate, zinc pyrrolidonecarboxylate, zinc L-pyrrolidonecarboxylate, zinc DL-pyrrolidonecarboxylate, magnesium pyrrolidonecarboxylate, magnesium L-pyrolidonecarboxylate, magnesium DL-pyrrolidonecarboxylate, calcium pyrrolidonecarboxylate, calcium L-pyrrolidonecarboxylate, calcium DL-pyrrolidonecarboxylate, aluminum pyrrolidonecarboxylate, aluminum L-pyrrolidonecarboxylate, aluminum DL-pyrrolidonecarboxylate, magnesium gluconate, zinc gluconate, magnesium gluconate, zinc lactate, magnesium lactate, calcium lactate, ethylenediamine diacetate, propylenediamine diacetate, and the like. These may be used either singly or in admixture of two or more selected from the foregoing group. Especially in view of obtaining a low temperature-stable creamy wash composition which is stable either at room temperature or at a high temperature, a salt made of a divalent cation and a monovalent or higher anion is preferable. A calcium salt, a magnesium salt, and a zinc salt are more preferable, and calcium chloride, magnesium chloride, and zinc pyrrolidonecarboxylate are especially preferable.

The water used as component (E) used in the invention is not particularly limited generally so long as it has a purity appropriate for use in washes or toiletries. Specifically, deionized water, well water, natural water, underground water, city water, hard water, soft water, and the like are available. These may be used either singly or in admixture of two or more selected from the foregoing group. In view of storage stability and sanitation of the invention product, deionized water is preferable.

The weight ratio of component (A) to component (C) used in the present invention is usually from 95:5 to 50:50. When the weight ratio of component (C) to component (A) is less than 5:95, the improvement in low temperature storage stability is low. When the weight ratio of component (C) to component (A) is more than 50:50, the foaming speed is low. In view of satisfying excellent low temperature storage stability and an excellent feeling upon use, the weight ratio of (A):(C) is preferably from 90:10 to 65:35, more preferably from 85:15 to 60:40.

The weight ratio of component (A) to component (D) used in the present invention is usually from 99.9:0.1 to 70:30. When the weight ratio of component (D) to component (A) is less than 0.1:99.9, a low temperature-stable creamy composition which is stable at room temperature is hardly obtained. When the weight ratio of component (D) to component (A) is more than 30:70, there is the problem that the composition is hardened at a low temperature. In view of obtaining a low temperature-stable creamy state which is stable even at room temperature, the weight ratio of (A):(D) is preferably from 99:1 to 75:25, especially preferably from 95:5 to 80:20.

The total amount of component (A), component (C), and component (D) used in the invention is usually from 10 to 40% by weight based on the total weight of the low temperature-stable creamy wash composition. When the total amount of component (A), component (C), and component (D) is less than 10% by weight, foaming is decreased thereby deteriorating the feeling upon use. When the total amount of component (A), component (C), and component (D) is more than 40% by weight, there is a problem that the composition is hardened at room temperature and a low temperature. In view of obtaining a good feeling upon use and a stable creamy state at room temperature and at low temperature, the total amount of (A), (C), and (D) is preferably from 12 to 35% by weight, especially preferably from 15 to 30% by weight.

Component (B) used in the present invention is usually present in an amount of from 10 to 50% by weight based on the total weight of the low temperature-stable creamy wash composition. When the amount of component (B) is less than 10% by weight, the composition tends to be liquefied at room temperature and a high temperature (40° C.), so that a creamy state might not be maintained. When the amount of component (B) is more than 50% by weight, foaming might be decreased to decrease the feeling upon use, or the composition might be hardened at a low temperature. In view of obtaining a stable creamy state at a low temperature, room temperature, and a high temperature, the amount of (B) is preferably from 15 to 40% by weight, especially preferably from 20 to 35% by weight.

The amount of Component (E) used in the present invention is usually from 10 to 70% by weight based on the total weight of the low temperature-stable creamy wash composition. When the amount of component (E) is less than 10% by weight, the composition might be hardened at room temperature and a low temperature, and the amount might be insufficient for dissolving components (A), (C), and (D). When the amount of component (E) is more than 70% by weight, the composition tends to be liquefied at room temperature and at a high temperature (40° C.), so that a creamy state might not be maintained. In view of providing a stable creamy state at a low temperature, room temperature, and a high temperature, the amount of (E) is preferably from 20 to 65% by weight, especially preferably from 30 to 60% by weight.

In a process for producing the low temperature-stable creamy wash composition in the present invention, predetermined amounts of component (A), component (B), component (C), and component (E) are mixed, and melt-dissolved at a temperature of from 60 to 80° C., and component (D) is then further added to give a uniform solution. Subsequently, the solution is cooled to room temperature to obtain the low temperature-stable creamy wash composition. When expansion occurs in dissolving them, a vacuum emulsifier or the like may be used.

Pearling agents such as polyethylene glycol monostearate, glycol stearate, glycol distearate, polyethylene glycol distearate, ethanolamide palmitate, and polyethylene glycol diisostearate can further be incorporated in the low temperature-stable creamy wash composition of the invention as component (F). These may be used either singly or in admixture of two or more selected from the foregoing group. Of these, glycol distearate is preferable in view of the fact that excellent temperature stability and pearly gloss can be imparted.

A soft creamy state can be retained at a high temperature by incorporating component (F) in the low temperature-stable creamy wash composition of the invention. Component (F) is ordinarily used in an amount of from 0.2 to 5% by weight based on the total weight of the low temperature-stable creamy wash composition. When the amount of component (F) is less than 0.2% by weight, there is a problem that the pearl appearance is hardly obtained. When the amount of component (F) is more than 5% by weight, there is a problem that the composition is hardened at a low temperature. In view of obtaining excellent temperature stability, the amount of (F)

is preferably from 0.5 to 3.0% by weight, especially preferably from 1 to 2.5% by weight.

Xanthane gum, hydroxypropyl starch phosphate, and carrageenan may be incorporated in the low temperature-stable creamy wash composition as component (G). These may be used either singly or in admixture of two or more selected from the foregoing group.

It is possible to decrease the difference between the hardness at a low temperature and the hardness at a high temperature and also to increase the foam quality by incorporating component (G) in the low temperature-stable creamy wash composition of the invention. The amount of component (G) is not particularly limited. It is preferably from 0.05 to 5.0% by weight, more preferably from 0.1 to 1.0% by weight, based on the total weight of the low temperature-stable creamy wash composition. When the amount of component (G) is less than 0.05% by weight, no satisfactory effect of improvement in hardness is provided. When it is more than 5.0% by weight, foaming is slowed to decrease feeling upon use.

The low temperature-stable creamy wash composition of the present invention can properly contain, in addition to the foregoing essential components, various optional components used in ordinary toiletries, quasi-drugs and the like unless the effects of the invention are impaired. Specific examples thereof include oils (camellia oil, corn oil, olive oil, rapeseed oil, coconut oil, palm oil, hardened castor oil, beeswax, liquid lanolin, liquid paraffin, squalene, vaseline, linear polysiloxanes such as dimethylpolysiloxane, cyclic polysiloxanes such as octamethylcyclotetrasiloxane, amino-modified silicone oil, and the like), surfactants (ionic surfactants such as alkyl sulfates, alkyl ether sulfates, fatty acid salts, sulfosuccinates, α-olefin sulfonates, N-acyl sarcosinates, N-acylmethyl taurates, alkyl ether carboxylates, and phosphates; imidazoline-based amphoteric surfactants; betaine-based amphoteric surfactants; and nonionic surfactants such as alkyl polyglycosides), thickening agents (high-molecular thickening agents such as guar gum, starch, ethylcellulose, methylhydroxypropyl starch, carboxymethylcellulose, carboxyvinyl polymer, bentonite, and hectorite), chelating agents, antiseptics, perfumes, ultraviolet absorbers, humectants, physiologically active components, antioxidants, anti-inflammatory agents, antimicrobial agents, antiperspirants, neutralizing agents, pH adjustors and the like. These can be incorporated according to the specific usage or dosage form of washes or toiletries.

The term "low temperature-stable creamy wash composition" in the present invention refers to, in a narrow sense, a composition comprising components (A) to (E) alone, whereas it refers to, in a wide sense, a composition comprising essential components (A) to (E) and further components (F) and (G) and other components which are contained therein unless impairing the effects of the invention. In the latter case, it corresponds to commercial toiletries, and is not particularly limited. Specifically, skin washes such as a creamy makeup remover, a creamy body wash and a cleansing foam and hair washes such as a creamy hair shampoo can be provided.

A composition which is somewhat different from the region of the invention but shows properties of the low temperature-stable creamy wash composition must be deemed to fall under the scope of the invention.

The compositions of the present invention are particularly useful for washing various parts of the human body, including the skin and hair of the human body. The compositions of the present invention may be applied directly to skin and/or hair which is dry to the touch. Alternatively, the composition may be applied to skin and/or hair which has already been wetted. In another embodiment, the composition may be mixed with water prior to application to the skin and/or hair. The washing with the present composition may further comprise rubbing the composition on the skin and/or hair to create lather or foam. Afterwards, the composition may be removed from the skin and/or hair by use of a cloth or towel or by rinsing with water.

Other features of the invention will become apparent in the course of the following descriptions of exemplary embodiments which are given for illustration of the invention and are not intended to be limiting thereof.

EXAMPLES

Examples 1 to 7 and Comparative Examples 1 to 8

Low temperature-stable creamy wash compositions (Examples 1 to 7) according to formulations shown in Table 1, and creamy wash compositions (Comparative Examples 1 to 6) and wash compositions (Comparative Examples 7 and 8) according to formulations shown in Tables 2 and 3 were prepared, and the hardness was evaluated at a low temperature (0° C.), room temperature (25° C.), and a high temperature (40° C.) by the following method.

Method for Measuring Hardness of a Creamy Wash Composition.

The prepared creamy wash composition was filled into a 50 mL glass vial (diameter 3.5 cm) to a height of 4 cm, and allowed to stand still at 0° C., 25° C., and 40° C. for 24 hours. A load test was conducted with a FUDO RHEOMETER (NRM-2010J-CW) and a flat cylindrical adapter (diameter 1.5 cm) at a table speed of 2 cm, and a load value (g) after 30 seconds was defined as the hardness of the creamy wash composition at each temperature.

Evaluation of the Hardness of a Creamy Wash Composition at Low Temperature.

The hardness (g) of a creamy wash composition at a low temperature (0° C.) was evaluated from the results of the load test according to the following criteria:
OO: 5 to 150
O: 151 to 250
Δ: 251 to 350
x: 351 or more Evaluation of Change in Hardness of a Creamy Wash Composition at Room Temperature and a Low Temperature.

From the results of the load test, a ratio of the hardness (g) at 0° C./the hardness (g) at 25° C.) was calculated, and a change in hardness of a creamy wash composition at room temperature (25° C.) and a low temperature (0° C.) was evaluated according to the following criteria:
OO: 0.5 to 1.4
O: 1.5 to 2.4
Δ: 2.5 to 3.4
x: 3.5 or more Evaluation of Feeling Upon Use of a Creamy Wash Composition.

As for the feeling upon use of the resulting creamy wash composition, an organoleptic evaluation was conducted by three expert panelists according to the following criteria. That is, an overall evaluation was conducted on four items: extension of cream, foaming speed, amount of foam, and moist feeling after drying. The average values of scores given by the three panelists were calculated. A score of at least 0 but less than 1 was defined as x, a score of at least 1 but less than 2 was defined as Δ, a score of at least 2 but less than 3 was defined as 0, and a score of at least 3 but at most 4 was defined as OO.

Score:
4: Four items are all good.
3: Three items are good.
2: Two items are good.
1: One item is good.
0: There is no good item.

TABLE 1

| Amount (Wt. %) | Ex. 1 | Ex. 2 | Ex. 3 | Ex. 4 | Ex. 5 | Ex. 6 | Ex. 7 |
|---|---|---|---|---|---|---|---|
| Sodium lauroyl glutamate | 16.0 | 16.0 | 18.0 | 20.0 | 16.0 | 16.0 | 16.0 |
| Glyceryl laurate | 4.0 | 4.0 | 5.0 | — | 4.0 | 4.0 | 4.0 |
| Glyceryl caprate | — | — | — | 5.0 | — | — | — |
| Magnesium chloride (6-hydrate) | 3.0 | 3.0 | 3.0 | 3.0 | 3.0 | 3.0 | 3.0 |
| Glycerin | 30.0 | 30.0 | 30.0 | 40.0 | 30.0 | 30.0 | 30.0 |
| Glycol distearate | — | 2.0 | 2.0 | 2.0 | 2.0 | 2.0 | 2.0 |
| Xanthane gum | — | — | — | — | 0.2 | — | — |
| Hydroxypropyl starch phosphate | — | — | — | — | — | 0.2 | — |
| Carrageenan | — | — | — | — | — | — | 0.2 |
| Water | 47.0 | 45.0 | 42.0 | 30.0 | 44.8 | 44.8 | 44.8 |
|  | 100.0 | 100.0 | 100.0 | 100.0 | 100.0 | 100.0 | 100.0 |
| Measurement results |  |  |  |  |  |  |  |
| Hardness at 0° C. | 188 | 175 | 230 | 142 | 119 | 122 | 98 |
| Hardness at 25° C. | 153 | 127 | 130 | 123 | 54 | 57 | 40 |
| Hardness at 40° C. | 10 | 13 | 15 | 21 | 10 | 11 | 9 |
| 0° C./25° C. hardness ratio | 1.2 | 1.4 | 1.8 | 1.2 | 2.2 | 2.1 | 2.4 |
| Evaluation results |  |  |  |  |  |  |  |
| Hardness at low temperature | ◯ | ◯ | ◯ | ◯◯ | ◯◯ | ◯◯ | ◯◯ |
| Change in hardness at low temperature and room temperature | ◯◯ | ◯◯ | ◯◯ | ◯◯ | ◯ | ◯ | ◯ |
| Feeling upon use | ◯◯ | ◯◯ | ◯◯ | ◯◯ | ◯◯ | ◯◯ | ◯◯ |

TABLE 2

| Amounts (Wt. %) | Comparative Example 1 JP-A-62-124200 | Comparative Example 2 JP-A-1-294799 | Comparative Example 3 JP-A-1-294799 |
|---|---|---|---|
| Sodium lauroyl glutamate | 24.0 | — | 25.0 |
| Sodium myristoyl glutamate | — | 25.0 | — |
| Glycerin | 12.0 | 15.0 | — |
| Butylene glycol | — | — | 25.0 |
| Sodium lauroylmethylalanine | 15.0 | — | — |
| Sodium lauroamphoacetate | — | 2.0 | 2.5 |
| Lauramide DEA | 6.0 | — | 3.0 |
| Glyceryl stearate | 5.0 | — | — |
| Polysorbate 60 | 5.0 | — | — |
| Glycereth-25 PCA Isostearate | 6.0 | — | — |
| Sodium chloride | 3.0 | — | — |
| PEG-50 distearate | — | — | 3.0 |
| Perfume | — | — | 0.1 |
| Water | 24.0 | 58.0 | 41.4 |
|  | 100.0 | 100.0 | 100.0 |
| Measurement results |  |  |  |
| Hardness at 0° C. | 733 | 391 | 462 |
| Hardness at 25° C. | 176 | 142 | 153 |
| Hardness at 40° C. | 36 | 123 | 33 |
| 0° C./25° C. hardness ratio | 4.2 | 2.8 | 3.0 |
| Evaluation results |  |  |  |
| Hardness at low temperature | XX | X | XX |
| Change in hardness at low temperature and room temperature | XX | Δ | Δ |
| Feeling upon use | Δ | ◯ | ◯ |

TABLE 3

| Amounts (Wt. %) | Comp. Ex. 4 | Comp. Ex. 5 | Comp. Ex. 6 | Com. Ex. 7 | Comp. Ex. 8 |
|---|---|---|---|---|---|
| Sodium lauroyl glutamate | 16.0 | 16.0 | 16.0 | 16.0 | 16.0 |
| Glyceryl laurate | — | — | — | 4.0 | 4.0 |
| Glyceryl caprate | — | — | — | — | — |
| Magnesium chloride (6-hydrate) | — | 3.0 | 3.0 | — | — |
| Glycerin | 30.0 | 30.0 | 30.0 | 40.0 | 30.0 |

TABLE 3-continued

| Amounts (Wt. %) | Comp. Ex. 4 | Comp. Ex. 5 | Comp. Ex. 6 | Com. Ex. 7 | Comp. Ex. 8 |
| --- | --- | --- | --- | --- | --- |
| Glycol distearate | — | — | 2.0 | — | 2.0 |
| Water | 54.0 | 51.0 | 49.0 | 40.0 | 48.0 |
|  | 100.0 | 100.0 | 100.0 | 100.0 | 100.0 |
| Measurement results |  |  |  |  |  |
| Hardness at 0° C. | 288 | 435 | 361 | 354 | 243 |
| Hardness at 25° C. | 114 | 162 | 128 | separated | liquefied |
| Hardness at 40° C. | 16 | 34 | 19 | liquefied | liquefied |
| 0° C./25° C. hardness ratio | 2.5 | 2.7 | 2.8 | — | — |
| Evaluation results |  |  |  |  |  |
| Hardness at low temperature | Δ | X | X | X | Δ |
| Change in hardness at low temperature and room temperature | Δ | Δ | Δ | — | — |
| Feeling upon use | ○ | ○ | ○ | — | — |

As is apparent from the results in Table 1, a low temperature-stable creamy wash composition having excellent feeling upon use could be obtained by combining a N-long-chain-acyl acidic amino acid and/or its salt as component (A), a polyhydric alcohol as component (B), a nonionic surfactant as component (C), a salt made of the divalent or higher cation and the monovalent or higher anion as component (D) and water as component (E). Further, a low temperature-stable creamy wash composition with decreased in hardness at room temperature could be obtained by incorporating xanthan gum, hydroxypropyl starch phosphate, or carrageenan as component (G) (see, Examples 5 to 7).

As is apparent from the results in Table 2, the composition was notably hardened at a low temperature (0° C.) in Comparative Example 1 (corresponding to JP-A-62-124200). As an approach to improve this, sodium lauroamphoacetate (N-carboxymethyl-N-hydroxyethylimidazolinium betaine) was incorporated in Comparative Example 2 (corresponding to JP-A-1-294799) and Comparative Example 3 (corresponding to JP-A-1-294799), so that the low temperature stability was slightly improved. However, the composition was far from a low temperature-stable creamy wash composition.

As is clear from Table 3, in the case of adding only the nonionic surfactant as component (C) to the N-acyl glutamic acid and/or its salt as component (A), the polyhydric alcohol as component (B) and water as component (E) (Comparative Examples 7 and 8), the composition was liquefied at room temperature, and no creamy wash composition was obtained. In the case of adding the salt made of the divalent or higher cation and the monovalent or higher anion alone as component (D) (Comparative Examples 5 and 6), the hardness at a low temperature was not satisfactorily improved. In view of the foregoing, by the present invention, it was possible to obtain the low temperature-stable creamy wash composition by combining components (A), (B), (C), (D) and (E), which could not have been achieved by the ordinary technique.

Formulation Examples 1 to 3

When low temperature-stable creamy wash compositions having formulations shown in Tables 4 to 6 below were prepared in a usual manner, excellent feeling upon use and excellent low temperature stability could be exhibited.

TABLE 4

Formulation Example 1 Cleansing foam

|  | (wt. %) |
| --- | --- |
| Sodium lauroyl glutamate (component (A)) | 16.0 |
| Sodium lauroyl aspartate (component (A)) | 2.0 |
| Glycerin (component (B)) | 30.0 |
| Butylene glycol (component (B)) | 2.0 |
| Glyceryl laurate (component (C)) | 5.0 |
| Magnesium chloride (6-hydrate)(component (D)) | 3.0 |
| Zinc PCA (component (D)) | 0.2 |
| Glyceryl distearate (component (F)) | 2.0 |
| Sodium Cocoyl Glycinate | 1.0 |
| Coco-glucoside | 1.0 |
| Sodium cocoylmethyltaurate | 2.0 |
| Cocamidopropyl betaine | 1.0 |
| PCA-Na (50%) | 1.0 |
| PEG-7 glyceryl cocoate | 0.5 |
| Disodium EDTA | 0.05 |
| Carrageenan (component (G)) | 0.2 |
| Water (component (E)) | 33.05 |

TABLE 5

Formulation Example 2 Creamy makeup remover

|  | (wt. %) |
| --- | --- |
| Sodium lauroyl glutamate (component (A)) | 18.0 |
| Sodium myristoyl glutamate (component (A)) | 1.0 |
| Glycerin (component (B)) | 30.0 |
| Glyceryl caprate (component (C)) | 5.0 |
| Magnesium chloride (6-hydrate)(component (D)) | 3.0 |
| Calcium chloride (component (D)) | 0.5 |
| Glycol distearate (component (F)) | 2.0 |
| PEG-60 hydrogenated castor oil | 1.0 |
| Polyquaternium-7 | 0.2 |
| Carbomer | 0.05 |
| Lauroyl lysine | 0.05 |
| Sodium Cocoyl Alaninate | 1.0 |
| Lauric acid | 0.2 |
| Di(phytosteryl/octyldodecyl)lauroyl glutamate | 0.2 |
| Serine | 0.1 |
| Proline | 0.1 |
| Mannitol | 0.1 |
| Citric acid | 0.1 |
| Preservatives | 0.3 |
| Water (component (E)) | 37.1 |

TABLE 6

Formulation Example 3 Creamy hair shampoo

| | (wt. %) |
|---|---|
| Sodium lauroyl glutamate (component (A)) | 15.0 |
| Sodium stearoyl glutamate (component (A)) | 2.0 |
| Glycerin (component (B)) | 35.0 |
| Glyceryl laurate (component (C)) | 4.5 |
| Butylene glycol laurate (component (C)) | 0.5 |
| Magnesium chloride (6-hydrate)(component (D)) | 3.0 |
| Zinc PCA | 0.1 |
| Glycol distearate (component (F)) | 2.0 |
| Polyquaternium-10 | 0.3 |
| Disodium EDTA | 0.05 |
| Sodium Lauroyl Sarcosinate | 2.0 |
| Dimethycone | 0.2 |
| Di(phytosteryl/octyldodecyl/behenyl) lauroyl glutamate | 0.2 |
| Polyquaternium-39 | 0.1 |
| Arginine | 0.02 |
| Allantoin | 0.1 |
| Perfume | 0.2 |
| Preservatives | 0.3 |
| Water (component (E)) | 34.43 |

INDUSTRIAL APPLICABILITY

The low temperature-stable wash composition and toiletries comprising a N-long-chain-acyl acidic amino acid and/or its salt and a polyhydric alcohol as active ingredients could stably be provided without impairing foaming property and feeling upon use.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A low temperature-stable creamy wash composition, which comprises:
   (A) at least one N-long-chain-acyl acidic amino acid or a salt thereof;
   (B) at least one polyhydric alcohol;
   (C) at least one nonionic surfactant;
   (D) at least one salt of magnesium and a monovalent or higher anion; and
   (E) water,
   wherein said wash composition has a hardness at 0° C. according to a load test with a Rheometer of from 5 to 250 (g) and a ratio of hardness at 0° C. to hardness at 25° C. of from 0.5 to 2.4.

2. A low temperature-stable creamy wash composition according to claim 1, wherein:
   said (A) at least one N-long-chain-acyl acidic amino acid or a salt thereof and said (C) at least one nonionic surfactant are present in a weight ratio of from 95:5 to 50:50;
   said (A) at least one N-long-chain-acyl acidic amino acid or a salt thereof and said (D) at least one salt of magnesium and a monovalent or higher anion are present in a weight ratio of from 99.9:0.1 to 70:30;
   said (A) at least one N-long-chain-acyl acidic amino acid or a salt thereof, said (C) at least one nonionic surfactant, and said (D) at least one salt of magnesium and a monovalent or higher anion are present in a total amount of from 10 to 40% by weight based on the total weight of said low temperature-stable creamy wash composition; and
   said (B) at least one polyhydric alcohol is present in an amount of from 10 to 50% by weight based on the total weight of said low temperature-stable creamy wash composition.

3. A low temperature-stable creamy wash composition according to claim 1, wherein said (A) at least one N-long-chain-acyl acidic amino acid or a salt thereof comprises at least one N-long-chain-acyl glutamic acid or a salt thereof.

4. A low temperature-stable creamy wash composition according to claim 2, wherein said (A) at least one N-long-chain-acyl acidic amino acid or a salt thereof comprises at least one N-long-chain-acyl glutamic acid or a salt thereof.

5. A low temperature-stable creamy wash composition according to claim 1, wherein said (C) at least one nonionic surfactant comprises at least one monoglyceryl mono-fatty acid ester.

6. A low temperature-stable creamy wash composition according to claim 2, wherein said (C) at least one nonionic surfactant comprises at least one monoglyceryl mono-fatty acid ester.

7. A low temperature-stable creamy wash composition according to claim 3, wherein said (C) at least one nonionic surfactant comprises at least one monoglyceryl mono-fatty acid ester.

8. A low temperature-stable creamy wash composition according to claim 4, wherein said (C) at least one nonionic surfactant comprises at least one monoglyceryl mono-fatty acid ester.

9. A method for making a composition according to claim 1, said method comprising:
   (i) mixing said (A) at least one N-long-chain-acyl acidic amino acid or a salt thereof, said (B) at least one polyhydric alcohol, said (C) at least one nonionic surfactant, and said (E) water, at a temperature of from 60 to 80° C., to obtain a mixture;
   (ii) adding said (D) at least one salt of magnesium and a monovalent or higher anion to said mixture, to obtain a solution; and
   (iii) cooling said solution is cooled to obtain said composition.

10. A method of washing the human body, said method comprising:
   (a) applying a composition according to claim 1 to at least a part of the human body.

* * * * *